(12) United States Patent
Kim et al.

(10) Patent No.: US 11,751,795 B2
(45) Date of Patent: Sep. 12, 2023

(54) PREDICTING DISEASE BY COMPARING VECTOR AND PERSON VECTOR EXTRACTED FROM BIOSIGNAL OF PERSON

(71) Applicant: KOREA INSTITUTE OF SCIENCE & TECHNOLOGY INFORMATION, Daejeon (KR)

(72) Inventors: Seonho Kim, Seoul (KR); Hong-Woo Chun, Seoul (KR); Jungjoon Kim, Seoul (KR); Byoung-Youl Coh, Seoul (KR)

(73) Assignee: KOREA INSTITUTE OF SCIENCE & TECHNOLOGY INFORMATION, Daejeon (KR)

( * ) Notice: Subject to any disclaimer, the term of this patent is extended or adjusted under 35 U.S.C. 154(b) by 493 days.

(21) Appl. No.: 16/800,818

(22) Filed: Feb. 25, 2020

(65) Prior Publication Data

US 2020/0268270 A1 Aug. 27, 2020

(30) Foreign Application Priority Data

Feb. 27, 2019 (KR) .......................... 10-2019-0023424

(51) Int. Cl.
*A61B 5/372* (2021.01)
*A61B 5/00* (2006.01)

(52) U.S. Cl.
CPC ............ *A61B 5/372* (2021.01); *A61B 5/7264* (2013.01); *A61B 5/4088* (2013.01)

(58) Field of Classification Search
CPC ..... A61B 5/372; A61B 5/7264; A61B 5/4088; A61B 5/316; A61B 5/369; A61B 5/7275; A61B 5/7267; G06N 20/00; G16H 50/20
See application file for complete search history.

(56) References Cited

U.S. PATENT DOCUMENTS

| | | | | |
|---|---|---|---|---|
| 2008/0004537 A1* | 1/2008 | Uutela | ................... | A61B 5/352 600/509 |
| 2008/0101665 A1* | 5/2008 | Collins | .................... | G06K 9/00 600/407 |
| 2016/0183812 A1* | 6/2016 | Zhang | ...................... | G07C 9/37 600/301 |
| 2018/0368699 A1* | 12/2018 | Kim | ..................... | A61B 5/6814 |
| 2019/0026430 A1* | 1/2019 | Grouchy | ............... | G06N 20/00 |

FOREIGN PATENT DOCUMENTS

| JP | 2017500991 A * | 7/2018 | ............. A61B 5/318 |
|---|---|---|---|
| KR | 101781024 B1 * | 9/2017 | ............. A61B 5/029 |

OTHER PUBLICATIONS

Kim, S. et al., "Wave2Vec: Vectorizing Electroencephalography Bio-Signal for Prediction of Brain Disease," International Journal of Environmental Research and Public Health, Aug. 15, 2018, 21 pages, vol. 15.

* cited by examiner

*Primary Examiner* — David D Davis
(74) *Attorney, Agent, or Firm* — WTA Patents

(57) ABSTRACT

Provided are a disease prediction apparatus and a disease prediction method using the same, which may easily learn a biosignal, may easily make a diagnosis, and may perform analysis in real time, in order to determine a disease using a biosignal via deep learning.

9 Claims, 5 Drawing Sheets

10

PREDICTING DISEASE BY COMPARING VECTOR AND PERSON VECTOR EXTRACTED FROM BIOSIGNAL OF PERSON

CROSS-REFERENCE TO RELATED APPLICATION

This application claims priority to Republic of Korea Patent Application No. 10-2019-0023424 filed on Feb. 27, 2019, which is incorporated by reference herein in its entirety.

BACKGROUND OF THE INVENTION

1. Field of the Invention

The present disclosure relates to an apparatus for predicting a disease and a method of predicting a disease using the same, and more particularly, to a technology that identifies a disease using a biosignal.

2. Description of the Prior Art

Research on a technology that measures various physical conditions of human bodies using biosignals is being conducted.

A biosignal may include, for example, an electroencephalogram (EEG) (or brainwaves), an electromyogram (EMG), an electrocardiography (ECG), or the like. An EEG refers to a waveform obtained by measuring a subtle change in electric potential using an electrode attached to the scalp, under conditions that a stimulus is applied to the cerebral cortex, an ionized current flows among nerve cells, and an electric field and a magnetic field are formed. Generally, the EEG is distributed in a frequency band of 0 to 100+ Hz, and an electric potential change is about dozens of $\mu V$. Accordingly, the EEG may be recorded by amplifying the electric potential change.

As an example of a technology that learns a biosignal measured in this manner and estimates a disease, a machine learning technology that uses artificial intelligence may be used. Particularly, the machine learning technology that uses artificial intelligence may learn a biosignal of a person which is a measured biosignal by using artificial intelligence, and may determine whether the person has a disease via learning.

However, the machine learning technology that uses artificial intelligence does not expose how a measured biosignal is determined as a patient biosignal and a non-patient biosignal, a diagnosis procedure, and the like. Therefore, the machine learning technology that uses artificial intelligence is inappropriate for making a medical diagnosis, which requires a description when making a decision on whether a subject has a disease using a measured biosignal.

Also, the machine learning technology may have difficulty in performing real-time analysis since the complexity in calculation of learning and diagnosis is high, and does not have a function of modeling and visualizing biosignal data, which is a drawback.

SUMMARY OF THE INVENTION

The present disclosure has been made in order to solve the above-mentioned problems in the prior art and an aspect of the present disclosure is to provide a disease prediction apparatus and a disease prediction method using the same, which may easily learn a biosignal to determine a disease, and may analyze a biosignal in real time to determine a disease, based on the learned biosignal.

In accordance with an aspect of the present disclosure, a disease prediction apparatus may include: a vector table obtaining unit configured to obtain a vector table including vectors, obtained by expressing a learning biosignal as multiple symbols according to a predetermined condition, and respectively expressing the multiple symbols as N-dimensional vectors; an extraction unit configured to extract a learning vector, which is learnable, by summing the N-dimensional vectors; and a prediction unit configured to predict a disease of a predetermined person by comparing the learning vector with a predetermined person vector extracted from a biosignal of the predetermined person.

The vector table obtaining unit is configured to obtain a predetermined person vector table including vectors, obtained by expressing the biosignal of the predetermined person as multiple symbols according to a predetermined condition, and respectively expressing the multiple symbols as N-dimensional vectors. The extraction unit is configured to extract the predetermined person vector by summing the N-dimensional vectors in the predetermined person vector table. The prediction unit is configured to predict a disease of the predetermined person by comparing the learning vector and the predetermined person vector.

The prediction unit is configured to predict a disease of the predetermined person, based on an angle between the learning vector and the predetermined person vector.

The learning vector includes a patient learning vector and a non-patient learning vector.

The prediction unit is configured to estimate that the predetermined person has a disease if an angle between the predetermined person vector and the non-patient learning vector is greater than an angle between the predetermined person vector and the patient learning vector.

The vector table obtaining unit is configured to obtain a time-based predetermined person vector table including vectors, obtained by expressing the predetermined person biosignal of a time period from a predetermined time ahead of a present time at which the predetermined person biosignal is input up to the present time, as multiple symbols, and respectively expressing the multiple symbols as N-dimensional vectors. The extraction unit is configured to extract a time-based predetermined person vector by summing the N-dimensional vectors in the time-based predetermined person vector table. The prediction unit is configured to compare an angle between the time-based predetermined person vector and the learning vector with a predetermined threshold angle over time, so as to determine whether the angle therebetween is less than the predetermined threshold angle.

The time-based predetermined person vector oscillates between the patient learning vector and the non-patient learning vector during a time period from the predetermined time ahead of the present time up to the present time, and the prediction unit is configured to estimate that the predetermined person has a disease if a distance between the time-based predetermined person vector and the patient learning vector is shorter than a distance between the time-based predetermined person vector and the non-patient learning vector, during the time period from the predetermined time ahead of the present time up to the present time.

The apparatus may further include a unit determination unit configured to segment the learning biosignal and the predetermined person biosignal according to a predetermined unit size according to a predetermined condition, and a symbol determination unit configured to assign a symbol to each predetermined unit.

The number of symbols increases as the unit size increases.

In accordance with an aspect of the present disclosure, a disease prediction method may include: obtaining a vector table including vectors, obtained by expressing a learning biosignal as multiple symbols according to a predetermined condition and respectively expressing the multiple symbols as N-dimensional vectors, and extracting a learning vector, which is learnable, by summing the N-dimensional vectors; obtaining a predetermined person vector table including vectors, obtained by expressing a biosignal of a predetermined person as multiple symbols according to a predetermined condition and respectively expressing the multiple symbols as N-dimensional vectors, and extracting a predetermined person vector by summing the N-dimensional vector; and predicting a disease of the predetermined person by comparing the learning vector and the predetermined person vector.

The operation of predicting a disease of the predetermined person by comparing the learning vector and the predetermined person vector may include predicting a disease of the predetermined person, based on an angle between the learning vector and the predetermined person vector.

The operation of extracting the learning vector may include extracting a patient learning vector and a non-patient learning vector.

The operation of predicting a disease of the predetermined person by comparing the learning vector and the predetermined person vector may include estimating that the predetermined person has a disease if an angle between the predetermined person vector and the non-patient learning vector is greater than an angle between the predetermined person vector and the patient learning vector.

A disease prediction apparatus and a disease prediction method using the same of the present disclosure may symbolize a biosignal, and may express the symbolized biosignal as a vector. The disease prediction apparatus may predict a disease by learning a biosignal expressed as a vector. Therefore, a learning scheme of a deep learning device which learns a biosignal may be simplified, which is advantageous.

Also, the disease prediction apparatus may learn a vectorized biosignal of a non-patient and a vectorized biosignal of a patient, and may determine whether a vectorized biosignal of a predetermined person is close to the vectorized biosignal of the non-patient person or the vectorized biosignal of the patient person, so as to identify a disease of the predetermined person. Accordingly, whether the predetermined person has a disease may be visually identified, which is advantageous.

Also, the disease prediction apparatus may vectorize a biosignal of a time period from a predetermined time ahead of the present time at which the biosignal is input up to the present time. Particularly, the disease prediction apparatus may vectorize a patient biosignal, a non-patient biosignal, and a predetermined person biosignal in a time period from a predetermined time ahead of the present time up to the present time, may compare angles among the vectorized patient biosignal, the vectorized non-patient biosignal, and the vectorized predetermined biosignal, and may identify, in real time, a vector which the vectorized predetermined person biosignal is closest to, which is advantageous.

BRIEF DESCRIPTION OF THE DRAWINGS

The above and other aspects, features and advantages of the present disclosure will be more apparent from the following detailed description taken in conjunction with the accompanying drawings, in which.

DETAILED DESCRIPTION OF THE EXEMPLARY EMBODIMENTS

Hereinafter, an embodiment of the present disclosure will be described with reference to the accompanying drawings.

Although a disease described in an embodiment of the present disclosure is considered to be dementia, it is apparent that overall diseases associated with the human body are predictable, in addition to the dementia.

Also, a biosignal described in an embodiment of the present disclosure may be one of an electroencephalogram (hereinafter, brainwaves), electrocardiographic waves, and the like, and the present disclosure is not limited by the type of biosignal.

Also, a disease prediction apparatus described in the embodiment of the present disclosure will be described with reference to one of the artificial intelligence devices capable of performing deep-learning.

Figure 1:
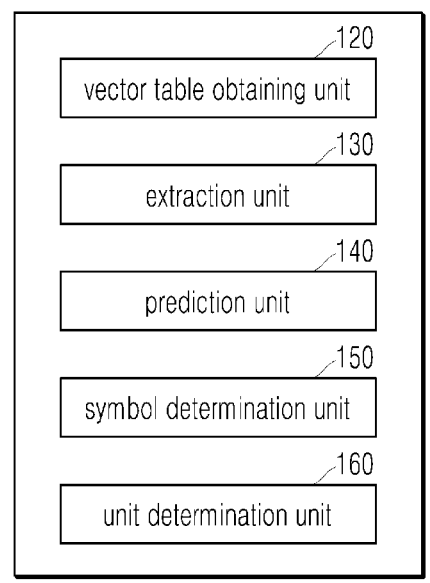
FIG. 1 is a schematic diagram of a disease prediction apparatus according to an embodiment of the present disclosure.
Figure 2:
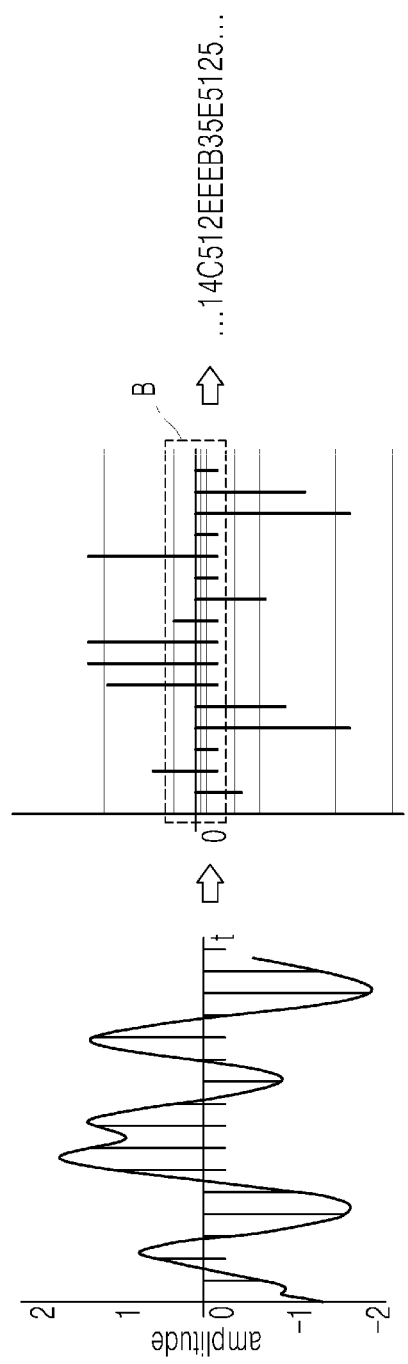
FIG. 2 is a diagram illustrating a process of expressing a biosignal as multiple symbols according to an embodiment of the present disclosure.
Figure 3:
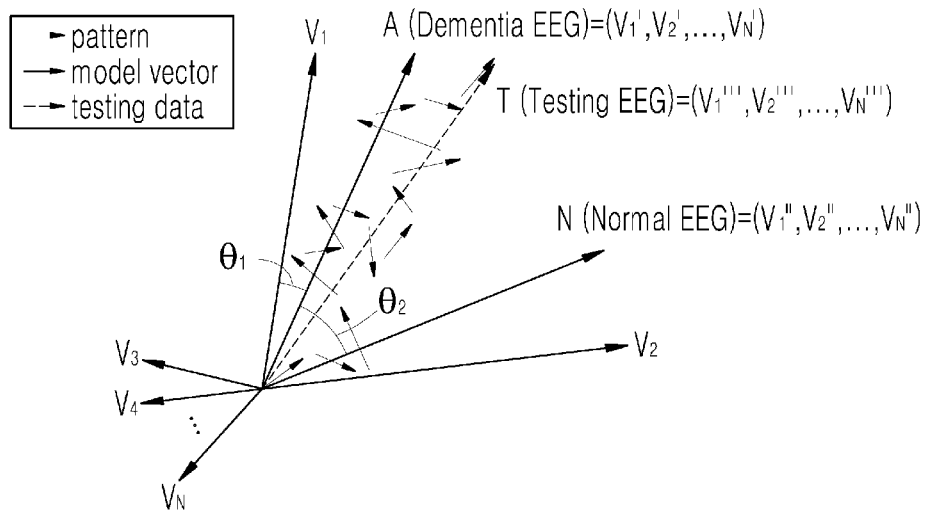
FIG. 3 is a diagram illustrating a vectorized biosignal according to an embodiment of the present disclosure.

FIG. 1 is a schematic diagram of a disease prediction apparatus according to an embodiment of the present disclosure. FIG. 2 is a diagram illustrating a process of expressing a biosignal as multiple symbols according to an embodiment of the present disclosure. FIG. 3 is a diagram illustrating a vectorized biosignal according to an embodiment of the present disclosure.

Before providing a detailed description with reference to drawings, note that a deep learning technology is a technology used for grouping or classifying objects or data. Particularly, machine learning refers to a technology in which a machine interprets data and automatically obtains an optimal feature. The machine learning may have a significantly high accuracy in detecting an optimal feature, which is advantageous.

However, the machine learning technology is inappropriate for a medical diagnosis device which learns a biosignal and determines whether a predetermined biosignal is a patient biosignal or a non-patient biosignal.

Particularly, the machine learning technology does not expose how a biosignal is learned and a criterion for determining whether an input biosignal corresponds to a patient or a non-patient. Therefore, the criterion for determining a patient using a biosignal is unclear, and the machine learning technology is inappropriate for a medical diagnosis machine, which is drawback.

Accordingly, an embodiment of the present disclosure provides a disease prediction apparatus and a disease prediction method using the same, which may learn a biosignal such as brainwaves, electrocardiogram, or the like via machine learning which is the deep learning technology, and may predict the probability of disease such as dementia or the like based on the learned information.

Referring to FIG. 1, a disease prediction apparatus 10 according to the present disclosure includes a vector table obtaining unit 120, an extraction unit 130, and a prediction unit 140.

The vector table obtaining unit 120 may obtain a vector table including vectors, which are obtained by expressing a learnable learning biosignal as multiple symbols according to a predetermined condition and respectively expressing the multiple symbols as N-dimensional vectors.

Particularly, a learnable learning biosignal is input to the disease prediction apparatus. In this instance, the disease prediction apparatus may not learn the input learning biosignal as it is, but may simplify and learn the same.

To this end, when a learning biosignal (see FIG. 2A) is input to the disease prediction apparatus, the disease prediction apparatus may segment and patternize the learning biosignal according to a predetermined time and a condition (see FIG. 2B).

In this instance, the condition used for segmenting the learning biosignal may be one of the various conditions according to the type of biosignal, the type of disease to be predicted, and the like, and an embodiment of the present disclosure will describe an example of performing segmentation according to a predetermined time.

Also, a learning biosignal segmented according to a predetermined time and condition may be expressed using various patterns, and a pattern may be one of the various patterns such as a line, a figure, and the like.

Each pattern of the segmented and patternized learning biosignal may be expressed as a symbol (see FIG. 2C). Each symbol may be one of a number, a character, and a combination of a number and a character. Hereinafter, an embodiment of the present disclosure provides an example of a combination of a number and an English character.

Each symbol of the symbolized learning biosignal may be expressed as an N-dimensional vector. Regarding the meaning of the N-dimensional vector, if each symbol is expressed as a 3-dimensional vector, symbol A may be expressed as (0, 1, 0). In this instance, the components of a vector may be configured according to the type of disease to be measured/predicted, the condition used for segmenting a learning biosignal, and the like. Hereinafter, the case in which each symbol has N components and is in 200-dimensions will be described.

A set of vectors obtained by expressing each symbol of the symbolized learning biosignal as an N-dimensional vector, may be referred to as a vector table.

In other words, a learning biosignal, which is input to the disease prediction apparatus in order to measure/predict a disease, is segmented, each segmented signal is patternized, each patternized signal is expressed as a symbol, and each symbol is expressed as an N-dimensional vector, whereby a vector table, which is a set of vectors may be obtained.

As described above, data to be learned may be simplified by vectorizing a biosignal. Therefore, a learning time spent when the deep learning device learns data may be minimized, and a learning efficiency of the deep learning device may be maximized.

In addition, a learning process may be visualized. That is, a biosignal may be symbolized according to a condition, the symbol is vectorized, and the vector is learned. Accordingly, all the processes of learning data may be visualized. Therefore, it is easy to describe whether a diagnosis of a disease is made using a biosignal, which is advantageous.

If a vector table is obtained based on a learning biosignal, the extraction unit 130 may extract a learning vector. Particularly, the extraction unit 130 may extract a learnable learning vector by summing N-dimensional vectors.

As described above, a learning biosignal may be expressed as multiple symbols, and each of the multiple symbols may be expressed as an N-dimensional vector having N components. A learning vector may be extracted by summing N-dimensional vector components of each of multiple symbols.

For example, if it is assumed that a symbolized learning biosignal is " . . . 14C512EEEB", symbol 1 is vector 1–(0, 0, 1), symbol A is vector 2–(0, 1, 0), symbol B is vector 3–(1, 0, 0), and the like, the extraction unit 130 may obtain (0, 0, 1)+(0, 1, 0)+(1, 0, 0) which is a sum of vector components of respective symbols.

As described above, a learning vector that is oriented in a predetermined direction may be extracted by summing all of the N-dimensional vectors. The extracted learning vector may be a criterion for estimating whether a predetermined person vector extracted from a biosignal of a predetermined person corresponds to a patient or a non-patient.

When the extraction unit 130 extracts a learning vector, the prediction unit 140 may compare the extracted learning vector and a predetermined person vector extracted from a biosignal of a predetermined person, which is input to the disease prediction apparatus, in the same manner as the above-mentioned scheme, so as to predict a disease of the predetermined person.

In this instance, the predetermined person vector may not be the same as the learning vector. That is, the learning biosignal and the predetermined person biosignal are different biosignals, and thus, the extracted learning vector and the extracted predetermined person vector are different vectors. However, whether the predetermined person vector is close to the learning vector may be determined based on the learning vector. If the predetermined person vector is close to the learning vector, the biosignal of the predetermined person is estimated to be similar to the learning biosignal.

For example, the angle between the learning vector and the predetermined person vector may be measured in order to predict a disease of the predetermined person. If the angle between the learning vector and the predetermined person vector is less than or equal to a predetermined threshold angle, it is determined that the learning vector and the predetermined person vector are close and the biosignal of the predetermined person is estimated to be similar to the learning biosignal.

In order to extract the learning vector and the predetermined person vector respectively from the learning biosignal and the predetermined person biosignal, the learning biosignal and the predetermined person biosignal may be segmented according to a predetermined unit size.

To this end, the disease prediction apparatus may further include a unit determination unit 160 configured to segment a biosignal according to a predetermined unit, and a symbol determination unit 150 configured to assign a symbol to each predetermined unit.

In this instance, in the process of symbolizing a biosignal, the number of symbols may increase as a predetermined unit size, which is used for segmenting the biosignal, increases.

Generally, the biosignal may be distributed to be close to the coordinate 0. Therefore, the biosignal adjacent to the coordinate 0 may be segmented in detail. Accordingly, a large number of symbols are assigned to data distributed close to the coordinate 0, wherein most data belongs to this case, and a large number of symbols may be obtained. A small number of symbols are assigned to data that is distributed far away from the coordinate 0, and a small number of symbols may be obtained.

Particularly, referring to area B of FIG. 2B, a change in the width is densely expressed as a coordinate is closer to the coordinate 0 and a change in the width is broadly expressed as a coordinate is further away from the coordinate 0. As described above, since a biosignal is generally distributed close to the coordinate 0, the purpose of the above-mentioned configuration is to symbolize a large amount of data which is close to the coordinate 0, wherein most data corresponds to this case.

To this end, previous statistical analysis associated with the overall biosignal is needed. That is, by identifying the normal distribution of the biosignal, a unit interval used for segmenting the biosignal may be determined. The unit interval for segmenting a biosignal which is obtained by a previous statistical analysis may be changed according to the type of biosignal, equipment (e.g., the resolution of a sensor or the like) that measures a biosignal, and the like, and an optimal variable may be determined via experimentation of an experimenter that measures a biosignal.

A process of predicting a disease of a predetermined person using a learning vector and a predetermined person vector extracted as described above, will be described.

Before providing a description, note that a patient learning vector A and a non-patient learning vector N may be extracted respectively from a patient biosignal and a non-patient biosignal, in the previous process of extracting a learning vector from a learning biosignal.

The extracted non-patient learning vector N and the patient learning vector A are learned. If a biosignal of a predetermined person is input to the disease prediction apparatus, the vector table obtaining unit 120 may obtain a predetermined person vector table. That is, the vector table obtaining unit 120 may obtain the predetermined person vector table including vectors which are obtained by expressing the input predetermined person biosignal as multiple symbols according to a predetermined condition and respectively expressing the multiple symbols as N-dimensional vectors.

Subsequently, the extraction unit 130 may sum all N-dimensional vector components in the predetermined person vector table, so as to extract a predetermined person vector T which is oriented in a predetermined direction.

If the predetermined person vector T is extracted, the prediction unit 140 may measure the angle between the patient learning vector A and the non-patient learning vector N. For example, if the angle $\theta_1$ between the predetermined person vector T and the patient learning vector A is less than the angle $\theta_2$ between the predetermined person vector T and the non-patient learning vector N, it is estimated that the predetermined person biosignal is similar to the patient biosignal. Accordingly, the predetermined person is estimated to be a patient.

The determination is made since multiple symbols extracted from the predetermined person biosignal are extracted to be a pattern similar to that of multiple symbols extracted from the patient biosignal. That is, when it is assumed that the biosignal of the patient is segmented and expressed as multiple symbols of " . . . 14C512EEEB", if it is identified that symbol EB is extracted and repeatedly extracted, among the symbols extracted from the patient biosignal, EB may be considered as the main symbol used for predicting a patient depending on whether the symbol EB is extracted.

When it is assumed that a biosignal of the predetermined person is segmented and expressed as multiple symbols "12C512ECEB", if the symbol EB is extracted from the predetermined person biosignal, a predetermined person vector T which is significantly similar to the patient learning vector A of the patient biosignal signal may be extracted, by taking into consideration the above-mentioned feature. Therefore, the predetermined person vector T may be expressed to be close to the patient learning vector A, and the predetermined person may be estimated to have a disease.

In this instance, the predetermined person is estimated to be a patient when the angle between the predetermined person vector T and the patient learning vector A is less than a threshold angle. The threshold angle may be, for example, an angle of 25 degrees, and the threshold angle may be differently set depending on a condition.

A predetermined person biosignal may be input to the disease prediction apparatus in real time. Therefore, the vector table obtaining unit 120 may obtain a time-based predetermined person vector table including vectors, obtained by expressing a predetermined person biosignal of a time from a predetermined period of time ahead of the present time at which the predetermined person biosignal of a predetermined person is input up to the present time, as multiple symbols and respectively expressing the multiple symbols as N-dimensional vectors.

Subsequently, the extraction unit 130 may extract a time-based predetermined person vector by summing all components of the N-dimensional vectors in the time-based predetermined vector table.

If the time-based predetermined person vector is extracted, the prediction unit 140 may perform comparison to determine whether the angle between the time-based predetermined person vector and the patient learning vector A or the angle between the time-based predetermined person vector and the non-patient learning vector N is less than a predetermined threshold angle, and may estimate whether the predetermined person has a disease.

Particularly, the time-based predetermined person vector may oscillates between the non-patient learning vector N and the patient learning vector A during a time from a predetermined period of time ahead of the present time at which the predetermined person biosignal is input up to the present time.

If the predetermined person has a disease, a predetermined symbol (e.g., symbol EB), which is extracted from a patient, may be extracted from the biosignal of the predetermined person, as described above. At the point in time at which the predetermined symbol is extracted, the angle between the time-based predetermined person vector of the predetermined person and the patient learning vector A may be less than a threshold angle.

Therefore, the time-based predetermined person vector is close to the patient learning vector A, and the prediction unit 140 may estimate that the predetermined person has a disease.

As described above, the disease prediction apparatus of the present disclosure is capable of making a diagnosis according to a time, and thus, whether the predetermined person has a disease may be identified in real time.

Figure 4:
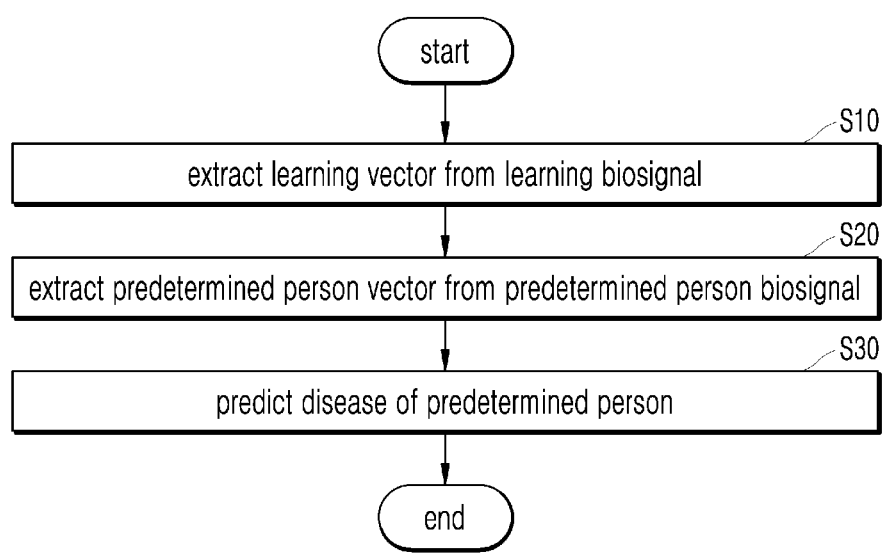
FIG. 4 is a flowchart illustrating a disease prediction method according to an embodiment.
Figure 5:
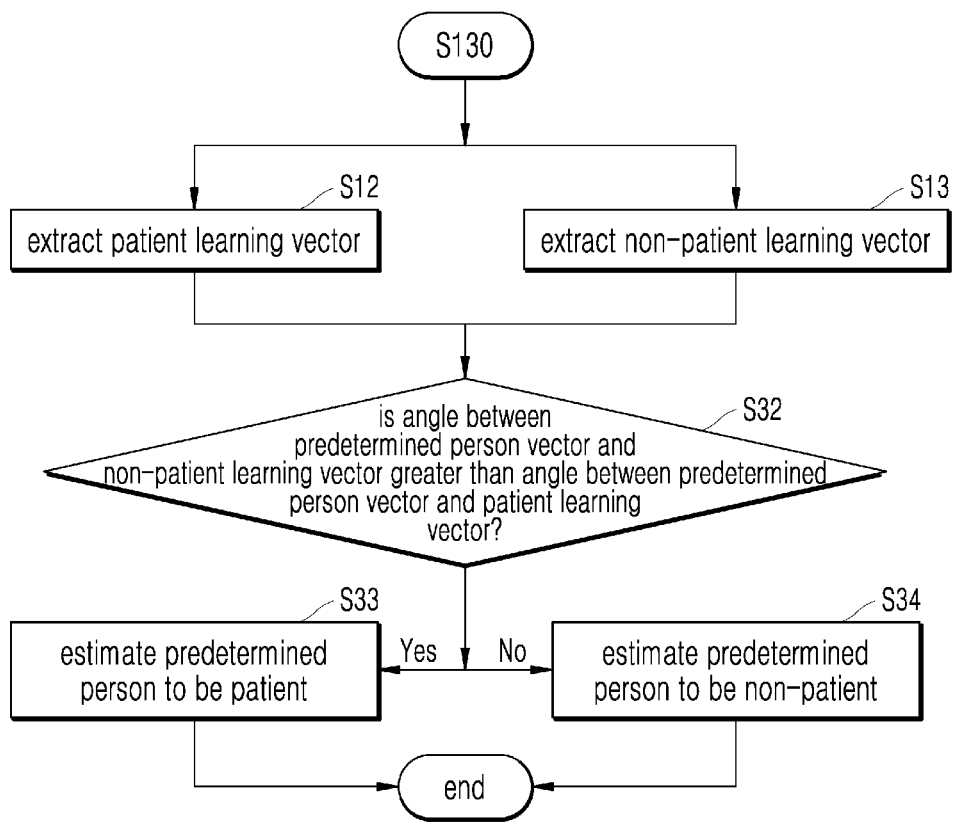
FIG. 5 is a flowchart illustrating a disease prediction method according to an embodiment of the present disclosure.

Hereinafter, a disease prediction method according to an embodiment of the present disclosure will be described with reference to FIGS. 4 and 5.

A method of predicting a disease via deep learning may obtain a vector table including vectors, obtained by expressing a learnable learning biosignal as multiple symbols according to a predetermined condition and respectively expressing the multiple symbols as N-dimensional vectors, and may extract a learnable learning vector by summing the N-dimensional vectors in operation S10.

Particularly, if a learning biosignal for learning a disease is input, the disease learning method may not learn the input learning biosignal as it is, but may simplify and learn the same.

To this end, if a learning biosignal is input, the method may segment and patternize the learning biosignal according to a predetermined time and condition.

The condition used for segmenting the learning biosignal may be one of the various conditions according to the type of biosignal, the type of disease to be predicted, and the like, and an embodiment of the present disclosure will describe an example of performing segmentation according to a predetermined period of time.

Each symbol of the symbolized learning biosignal may be expressed as an N-dimensional vector. Regarding the meaning of the N-dimensional vector, if each symbol is expressed as a 3-dimensional vector, symbol A may be expressed as (0, 1, 0).

A set of vectors obtained by expressing each symbol of the symbolized learning biosignal as an N-dimensional vector, may be referred to as a vector table.

If a vector table is obtained, a learnable learning vector may be extracted by summing N-dimensional vectors.

As described above, a learning biosignal may be expressed as multiple symbols, and each of the multiple symbols may be expressed as an N-dimensional vector having N components. A learning vector may be expressed by summing N-dimensional vector components of each of multiple symbols.

For example, if it is assumed that a symbolized learning biosignal is " . . . 14C512EEEB", symbol 1 is vector 1–(0, 0, 1), symbol A is vector 2–(0, 1, 0), symbol B is vector 3–(1, 0, 0), and the like, the extraction unit 130 may obtain (0, 0, 1)+(0, 1, 0)+(1, 0, 0) which is a sum of vector components of respective symbols.

As described above, a learning vector that is oriented in a predetermined direction may be extracted by summing all of the N-dimensional vectors. The extracted learning vector may be a criterion for estimating whether a predetermined person vector extracted from a biosignal of a predetermined person corresponds to a patient or a non-patient.

When a learning vector is extracted from a learning biosignal, a patient learning vector A and a non-patient learning vector N may be extracted respectively from a patient biosignal and a non-patient biosignal in operation S12 and operation S13.

Subsequently, a predetermined person vector table including vectors is obtained, the vectors being obtained by expressing a biosignal of a predetermined person as multiple symbols according to a predetermined condition and respectively expressing the multiple symbols as N-dimensional vectors, and a predetermined person vector is extracted by summing the N-dimensional vectors in operation S20. The predetermined person vector may be extracted in the same manner as the above-mentioned method of extracting the learning vector, and the predetermined person vector may be data to be used for predicting a disease of the predetermined person via comparison with the previously extracted learning vector.

Subsequently, by comparing the extracted learning vector and the predetermined person vector, whether the predetermined person has a disease may be estimated in operation S30.

Particularly, the predetermined person vector may not be the same as the learning vector. That is, the learning biosignal and the predetermined person biosignal are different biosignals, and thus, the extracted learning vector and the extracted predetermined person vector are different vectors. However, whether the predetermined person vector is close to the learning vector may be determined based on the learning vector. If the predetermined person vector is close to the learning vector, the biosignal of the predetermined person is estimated to be similar to the learning biosignal.

For example, the angle between the learning vector and the predetermined person vector may be measured in order to predict a disease of the predetermined person. If the angle between the learning vector and the predetermined person vector is less than or equal to a predetermined threshold angle, it is determined that the learning vector and the predetermined person vector are close and the biosignal of the predetermined person is estimated to be similar to the learning biosignal.

In other words, if the non-patient learning vector N, the patient learning vector A, and the predetermined person vector T are extracted, the angle between the predetermined person vector T and the patient learning vector A, and the angle between the predetermined person vector T and the non-patient learning vector N may be measured in operation S32.

In this instance, if the angle $\theta_1$ (see FIG. 3) between the predetermined person vector T and the patient learning vector A is less than the angle $\theta_2$ (see FIG. 2) between the predetermined person vector T and the non-patient learning vector N, it is estimated that the biosignal of the predetermined person is similar to the patient biosignal. Accordingly, the predetermined person is estimated to be a patient in operation S33.

Unlike the above, if the angle $\theta_1$ (see FIG. 3) between the predetermined person vector T and the patient learning vector A is greater than the angle $\theta_2$ (see FIG. 2) between the predetermined person vector T and the non-patient learning vector N, it is estimated that the predetermined person biosignal is similar to the non-patient biosignal. Accordingly, the predetermined person is estimated to be a non-patient in operation S34.

As described above, data to be learned may be simplified by vectorizing a biosignal. Therefore, a learning time spent when the deep learning device learns data may be minimized, and a learning efficiency of the deep learning device may be maximized.

In addition, a learning process may be visualized. That is, a biosignal may be symbolized according to a condition, and the symbol is vectorized, and the vector is learned. Accordingly, all the processes of learning data may be visualized. Therefore, it is easy to describe whether a diagnosis of a disease is made using a biosignal, which is advantageous.

The implementations of the functional operations and subject matter described in the present disclosure may be realized by a digital electronic circuit, by the structure described in the present disclosure, and the equivalent including computer software, firmware, or hardware including, or by a combination of one or more thereof. Implementations of the subject matter described in the specification may be implemented in one or more computer program products, that is, one or more modules related to a computer program command encoded on a tangible program storage medium to control an operation of a processing system or the execution by the operation.

A computer-readable medium may be a machine-readable storage device, a machine-readable storage substrate, a memory device, a composition of materials influencing a machine-readable radio wave signal, or a combination of one or more thereof.

In the specification, the term "system" or "device", for example, covers a programmable processor, a computer, or all kinds of mechanisms, devices, and machines for data processing, including a multiprocessor and a computer. The processing system may include, in addition to hardware, code that creates an execution environment for a computer program when requested, such as a code that constitutes processor firmware, a protocol stack, a database management system, an operating system, or a combination of one or more thereof.

A computer program (also known as a program, software, software application, script, or code) can be written in any form of programming language, including compiled or interpreted languages, declarative or procedural languages, and it can be deployed in any form, including as a stand-alone program or module, a component, subroutine, or another unit suitable for use in a computer environment. A computer program may, but need not, correspond to a file in a file system. A program can be stored in a single file provided to the requested program, in multiple coordinated files (for example, files that store one or more modules, sub-programs, or portions of code), or in a portion of a file that holds other programs or data (for example, one or more scripts stored in a markup language document). A computer program can be deployed to be executed on one computer or on multiple computers that are located at one site or distributed across a plurality of sites and interconnected by a communication network.

A computer-readable medium suitable for storing a computer program command and data includes all types of non-volatile memories, media, and memory devices, for example, a semiconductor memory device such as an EPROM, an EEPROM, and a flash memory device, and a magnetic disk such as an external hard disk or an external disk, a magneto-optical disk, a CD-ROM, and a DVD-ROM disk. A processor and a memory may be added by a special purpose logic circuit or integrated into the logic circuit.

The implementations of the subject matter described in the specification may be implemented in a calculation system including a back-end component such as a data server, a middleware component such as an application server, a front-end component such as a client computer having a web browser or a graphic user interface which can interact with the implementations of the subject matter described in the specification by the user, or all combinations of one or more of the back-end, middleware, and front-end components. The components of the system can be mutually connected by any type of digital data communication such as a communication network or a medium.

While the specification contains many specific implementation details, these should not be construed as limitations to the scope of any disclosure or of what may be claimed, but rather as descriptions of features that may be specific to particular embodiments of particular disclosures. Certain features that are described in the specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

In addition, in the specification, the operations are illustrated in a specific sequence in the drawings, but it should be understood that the operations are not necessarily performed in the shown specific sequence or that all shown operations are necessarily performed in order to obtain a preferable result. In a specific case, multitasking and parallel processing may be preferable. Furthermore, it should not be understood that a separation of the various system components of the above-mentioned implementation is required in all implementations. In addition, it should be understood that the described program components and systems usually may be integrated in a single software package or may be packaged in a multi-software product.

As described above, specific terms disclosed in the specification do not intend to limit the present disclosure. Therefore, while the present disclosure was described in detail with reference to the above-mentioned examples, a person skilled in the art may modify, change, and transform some parts without departing a scope of the present disclosure. The scope of the present disclosure is defined by the appended claims to be described later, rather than the detailed description. Accordingly, it will be appreciated that all modifications or variations derived from the meaning and scope of the appended claims and their equivalents are included in the range of the present disclosure.

What is claimed is:

1. An apparatus for predicting a disease, the apparatus comprising:
    a processor; and
    memory storing instructions thereon, the instructions when executed by the processor cause the processor to:
        segment a learning biosignal into segments according to time;
        patternize the segments of the learning biosignal;
        express each of the patternized segments to a symbol of an N-dimensional vector;
        obtain a vector table including N-dimensional vectors of the patternized segments;
        extract a learning vector by summing the N-dimensional vectors, the learning vector including a patient learning vector and a non-patient learning vector; and
        predict a disease of a predetermined person by comparing the learning vector with a predetermined person vector extracted from a biosignal of the predetermined person, the predetermined person determined to have a disease when an angle between the predetermined person vector and the non-patient learning vector is greater than an angle between the predetermined person vector and the patient learning vector.

2. The apparatus of claim 1, wherein the instructions further cause the processor to obtain a predetermined person vector table including N-dimensional vectors, the N-dimensional vectors being obtained by expressing the biosignal of the predetermined person as multiple symbols according to a predetermined condition, and respectively expressing the multiple symbols as N-dimensional vectors,
    wherein the predetermined person vector is extracted by summing the N-dimensional vectors in the predetermined person vector table, and
    wherein a disease of the predetermined person is predicted by comparing the learning vector and the predetermined person vector.

3. The apparatus of claim 2, wherein the disease of the predetermined person is predicted, based on an angle between the learning vector and the predetermined person vector.

4. The apparatus of claim 1, wherein the instructions cause the processor to obtain a time-based predetermined person vector table including N-dimensional vectors, N-dimensional vectors being obtained by expressing the predetermined person biosignal from a first time to a second time as multiple symbols, and respectively expressing the multiple symbols as N-dimensional vectors;
  wherein a time-based predetermined person vector is extracted by summing the N-dimensional vectors in the time-based predetermined person vector table, and
  wherein the instructions cause the processor to determine an angle between the time-based predetermined person vector and the learning vector is less than a predetermined threshold angle over time.

5. The apparatus of claim 4, wherein the time-based predetermined person vector oscillates between the patient learning vector and the non-patient learning vector during a time period from the first time and the second time, and
  wherein the instructions cause the processor to determine that the predetermined person has a disease when a distance between the time-based predetermined person vector and the patient learning vector is shorter than a distance between the time-based predetermined person vector and the non-patient learning vector during the time period from the first time and the second time.

6. The apparatus of claim 1, wherein the instructions further cause the processor to:
  segment the learning biosignal and the predetermined person biosignal according to a predetermined unit size according to a predetermined condition; and
  assign a symbol to each segment of the learning biosignal and the predetermined person biosignal.

7. The apparatus of claim 6, wherein a number of symbols increases as the unit size increases.

8. A method of predicting a disease, the method comprising:
  segmenting a learning biosignal into segments according to time;
  patternizing the segments of the learning biosignal;
  expressing each of the patternized segments to a symbol of an N-dimensional vector;
  obtaining a vector table including N-dimensional vectors of the patternized segments;
  extracting a learning vector by summing the N-dimensional vectors, the learning vector including a patient learning vector and a non-patient learning vector;
  obtaining a predetermined person vector table including N-dimensional vectors, N-dimensional vectors being obtained by expressing a biosignal of a predetermined person as multiple symbols according to a predetermined condition and respectively expressing the multiple symbols as N-dimensional vectors;
  extracting a predetermined person vector by summing the N-dimensional vectors; and
  predicting a disease of the predetermined person by comparing the learning vector and the predetermined person vector, the predetermined person determined to have a disease when an angle between the predetermined person vector and the non-patient learning vector is greater than an angle between the predetermined person vector and the patient learning vector.

9. The method of claim 8, wherein the predicting comprises:
  predicting a disease of the predetermined person, based on an angle between the learning vector and the predetermined person vector.

* * * * *